United States Patent [19]
Nunes et al.

[11] Patent Number: 5,878,607
[45] Date of Patent: Mar. 9, 1999

[54] SURGICAL CAST CUTTER

[75] Inventors: Victor M. Nunes, Cumberland, R.I.;
Edward H. Meisner, Short Hills, N.J.

[73] Assignee: Johnson & Johnson Professional, Inc., Raynham, Mass.

[21] Appl. No.: 499,097

[22] Filed: Jul. 6, 1995

[51] Int. Cl.[6] .................................................... B27B 9/00
[52] U.S. Cl. ............................................. 30/124; 30/391
[58] Field of Search ........................... 30/124, 133, 390, 30/391; 606/82, 179

[56] References Cited

U.S. PATENT DOCUMENTS

| | | | |
|---|---|---|---|
| 2,929,177 | 3/1960 | Sheps | 51/273 |
| 3,103,069 | 9/1963 | Gary | 30/124 |
| 5,213,913 | 5/1993 | Anthony et al. | 30/500 |

FOREIGN PATENT DOCUMENTS

| | | | |
|---|---|---|---|
| 55896 | 7/1982 | European Pat. Off. | 30/391 |
| 85/03473 | 8/1985 | WIPO | 30/391 |

*Primary Examiner*—Douglas D. Watts
*Attorney, Agent, or Firm*—Joseph F. Shirtz

[57] ABSTRACT

A cast saw for removing hard orthopaedic bandages, for example formed of plaster is disclosed. The cast saw is a unitary device containing a rechargeable battery pack in a removable filter form collection chamber. A shroud covers at least a portion of the saw blade and such shroud is movable by the cutting operation from the interference of the casting material as the blade is received within the casting material while cutting through such casting material. A dust channel is formed within the housing and dust and debris caused by the cutting operation is pulled through such dust channel by the forces applied by impeller rotated by an electric motor received within the housing. A pressure sensitive switch is supplied which senses an increase in force on the saw blade and increases the current supplied to the motor proportionally in order to provide additional torque to the motor.

8 Claims, 4 Drawing Sheets

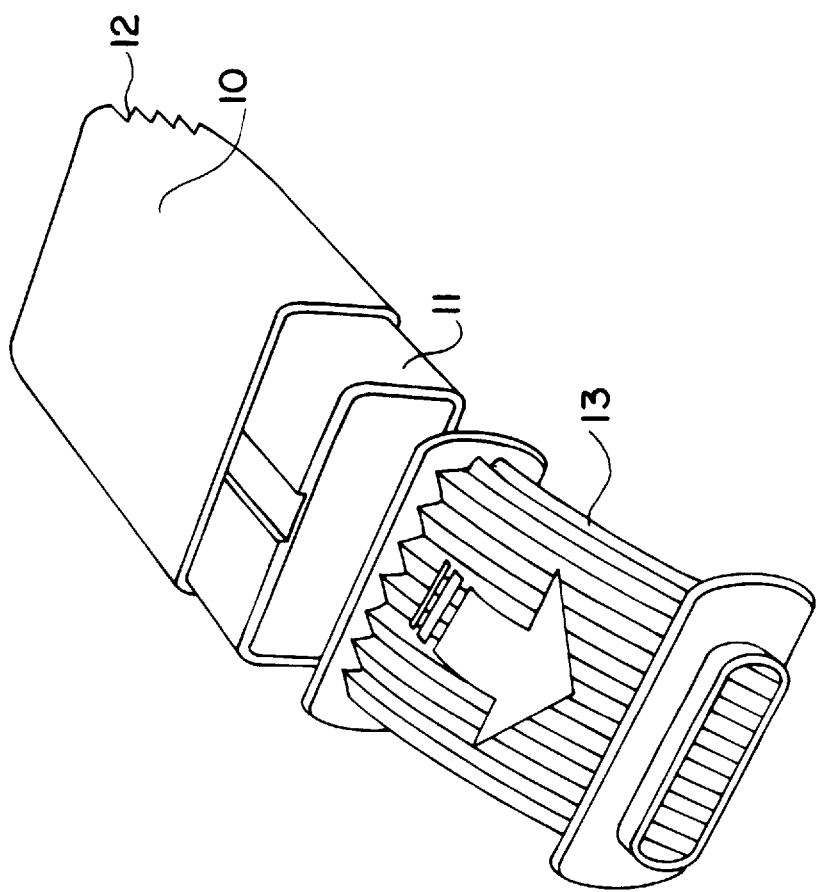

SURGICAL CAST CUTTER

BACKGROUND OF THE INVENTION

This invention relates to surgical instruments and particular to powered saws for the removal of orthopaedic bandages of the hard casting material type.

Portable cast cutters or saws have been known for many years and are formed having a small circular or part circular saw blade that oscillates through a limited angle to cut through a hard cast material such as plaster or a resinous material. The small angle oscillations, however, assure that the soft tissue of the patient wearing the cast will not be damaged. These oscillations are driven by a suitable transmission which may include various types of mechanical interconnections that are well known in the art. The transmission itself is normally driven by a small electric motor. During the cast removal operation there is a significant quantity of dust and debris generated by the operation. In order to remove this dust and debris it is known to connect the hose of a conventional vacuum cleaner to the saw itself. Such an arrangement is shown in U.S. Pat. No. 2,929,177. Other examples of fan-type dust and debris removal systems are shown in U.S. Pat. Nos. 3,103,069 and 3,481,036.

U.S. Pat. No. 4,421,111 discloses a low voltage surgical cast cutter with a vacuum exhaust of debris. This device is described as a surgical cast cutter or other power tool which contains a main tool section and a complimentary hose section releasably secured to the tool section at a rear end thereof. A low voltage electric motor in the tool section drives a transmission which oscillates a cutter mounted forwardly of the tool section. A debris conduit in the tool section communicates with an opening formed in the hose section when the sections are joined together. The hose section carries a flexible vacuum hose communicating with the opening therein, thereby facilitating removal of dust particles generated during operation of the cutter to remove, for example, a plaster cast. This device, however, is bulky and cumbersome to use as the vacuum attachment is separate from the cutter itself and rather large. This requires that a power pack or a vacuum source be attached to the device and positioned near the device.

SUMMARY OF THE INVENTION

The present invention calls for a saw for removing orthopaedic casting bandages which comprises a unified housing containing an electric motor therein. The electric motor has a rotating shaft which operates a saw blade. The operation of the saw blade may be through a suitable transmission to cause the blade to oscillate through the required angle and at the required speed relative to the speed of rotation of the motor. A blower is attached at one end of the motor shaft to provide a flow of air through the device. The flow of air is in a direction from an area surrounding the saw blade and into a collection zone or collection chamber which is partially defined by a filter material. The filter material permits the passage of air while trapping the entrained debris within the collection chamber.

The housing also defines a space for receiving a rechargeable battery pack for providing power to the electric motor. Both the battery pack and the collection chamber are removable from the saw. The battery pack is removable for recharging purposes or may be recharged while in place within the device and the collection chamber is removable for emptying purposes.

The saw is provided with a pressure sensitive switch for sensing the force supply to the saw blade during the cutting operation. This pressure sensitive switch directly controls the current supplied to the motor in order to maintain a sufficient torque to continue the cutting operation. That is, at idle the motor idles at a slow speed but increases as the pressure on the blade increases. The increase in the supply of current to the motor increases the torque and often increases the speed in order to provide sufficient power for difficult cutting operations. In the prior art, however, the devices merely attempted to maintain a constant speed at the motor no matter what the pressure was on the blade. This caused an overheating situation when extreme forces were applied to the blade.

The saw further includes a shroud covering most of the blade and forming a seal with the casting material during the cutting operation. In this way a smaller fan and collection chamber may be used eliminating the need for the large conventional vacuum used in prior art devices. The shroud may be made of an accordion-like material that collapses upon use of the saw such that the saw may pass into the relatively hard casting material while the shroud maintains a surface contact with the outer surface of the casting material. As the saw passes into the casting material in the cutting operation the saw extends out of the shroud and into the casting material thus providing that the shroud maintains its contact.

BRIEF DESCRIPTION OF THE DRAWINGS

The invention will now be described with reference to the attached figures wherein

FIG. 4 is a perspective view of the dust bin with filter material removed.

DETAILED DESCRIPTION OF THE PREFERRED EMBODIMENT

Figure 1:
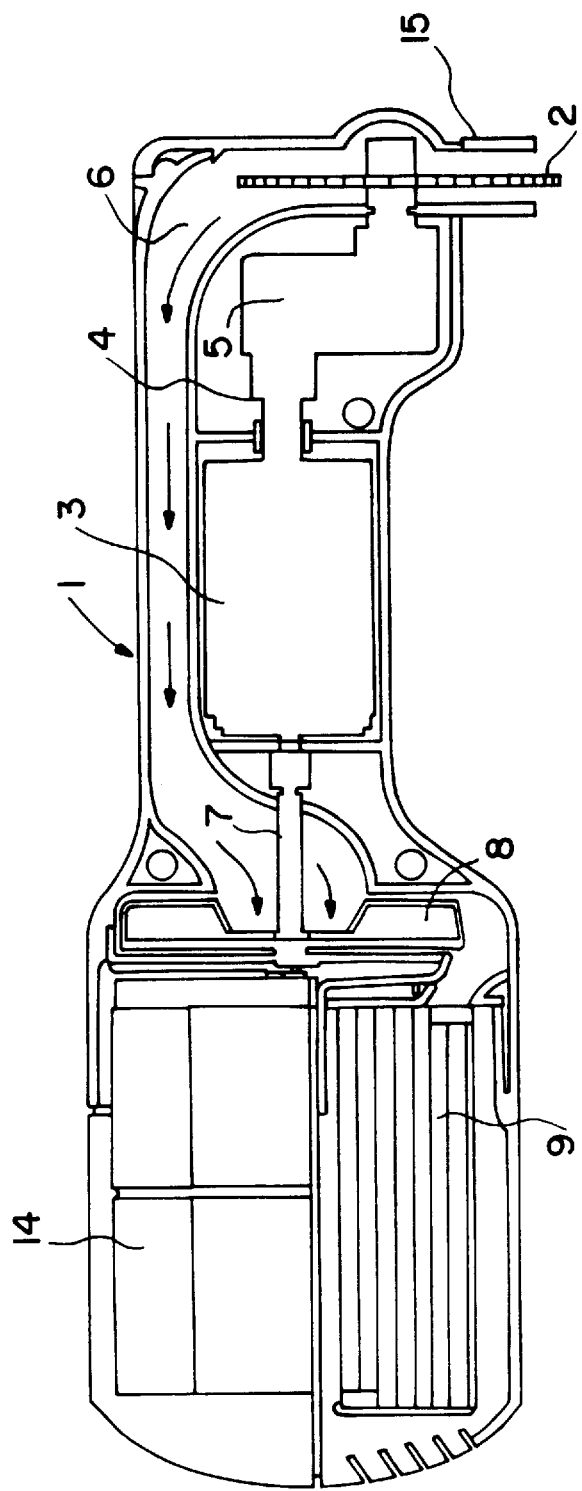
FIG. 1 is a longitudinal cross-sectional view of the saw of the present invention.

Referring to the figures there is a cast saw having a housing 1 (FIG. 1) which receives mounted thereon for rotation a blade 2. The blade is driven by an electric motor 3 which is a motor of 0.12 HP driven at a control voltage of 21.6 VDC. A forward shaft 4 extends towards the forward end of the housing 1 and is operably attached to a transmission 5 for transmitting the power from the forward shaft 4 to the blade 2.

Figure 2:
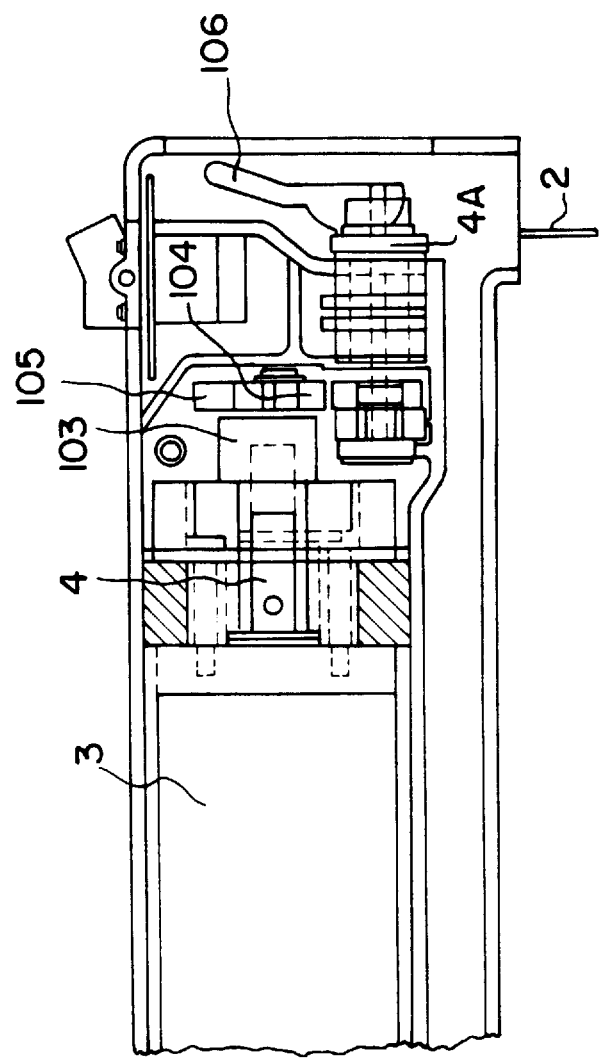
FIG. 2 is a schematic representation of the drive system of the saw of the present application.

The DC motor is the power source for driving the blade and fan for use of the cast saw. The forward shaft 4 (FIG. 2) has provided thereon a counter balance 103 to eliminate vibration. Forward of the counter balance 103 and connected to the drive shaft 4 is an eccentric drive bearing 104. The eccentric drive bearing 104 rotates 360° inside an oscillating box yolk 105. The oscillating box yolk is connected to the blade drive shaft 4A. The oscillating yolk moves in a 10° arc which turns the blade drive shaft in a 10° arc. The movement of the oscillating yolk and blade drive shaft moves the blade in a 10° arc. The blade is keyed to the blade drive shaft 4A in order to provide for transmission of this motion. This attachment mechanism may be for example a comb lock lever 106.

The blade 2 is, for example, per inch tooth blade of elliptical shape having 18 teeth around the outer circumference. The blade is made of stainless steel with a coating which decreases the blade wear. It is elliptical in overall shape, has a keyed attachment hole which fits onto the saw drive shaft. There are 18 teeth per inch on the lower section of the blade. The blade is provided with 3 through holes which reduce the mass of the blade and also allows for cast dust to pass through during vacuuming dust collection.

The housing 1 defines a dust channel 6 which directs the flow of debris ladened air as will be described below. A rearward shaft 7 extends rearward from the electric motor 3 and has mounted thereon an impeller or fan 8. The fan or impeller provides the force to the entraining air during operation of the device. When the electric motor 3 operates to spin the forward shaft 4 and the rearward shaft 7 this causes the blade 2 to operate as well as causes rotation of the fan or impeller 8. This causes a flow of air through the dust channel in a direction from the blade to the impeller. The dust channel 6 communicates with a collection chamber 9.

Figure 3:
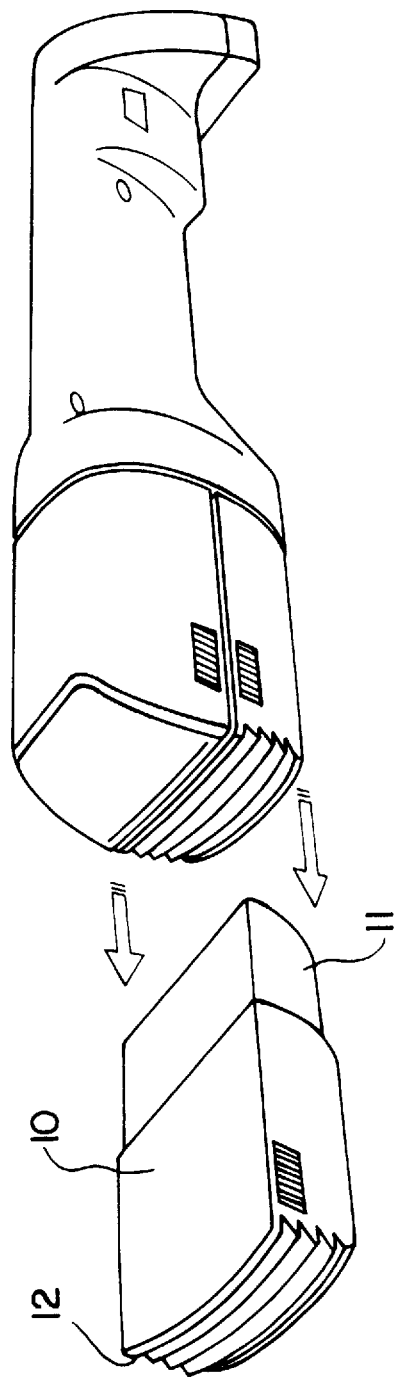
FIG. 3 is a perspective view of the cast saw of the present invention showing the removable dust bin.

The collection chamber 9 is formed from a removable part of the housing in the form of a dust bin 10 (FIG. 3). The dust bin 10 has a mounting portion 11 (FIG. 4) which is received within a space defined by the housing 1. A suitable mounting and locking structure is provided and is not shown. The dust bin 10 has a rear slotted wall 12 that permits passage of the air from the impeller or fan 8 after passage through the fan and dust bin 10. Received within the dust bin 10 is a disposable filter bag 13. The filter bag is formed of a filter material such as paper and is pleated in order to provide a large surface area to reduce the effects of the clogging of the debris received within the filter bag. After use the dust bin 10 may be removed from the housing 1 and the disposable filter bag 13 removed from the dust bin 10 for disposal. A new clean filter bag may then be placed within the dust bin 10 and the dust bin reattached having a clean filter material for the next operation.

The housing similarly receives a removable battery pack 14. The structure of the housing portion of the battery pack 14 is similar to that of the dust bin 10, however, the rear wall is not necessarily slotted unless necessary for heat dissipation. The battery pack 14 is similarly removable and is provided with an attachment mechanism having suitable coupling devices to couple the terminals of the battery pack to the terminals of the electric motor 3. The battery pack is formed of 18 battery units connected suitably to provide 21.6 volts and 3.6 amps of current. This battery pack may be provided with a suitable recharging attachment (not shown) which may be plugged into the battery pack while in the device or the device may be mounted upon for recharging of the battery pack. Alternatively, the battery pack may be removed and placed in a recharger for recharger or may be removed to have the batteries replaced in their entirety with new batteries.

The battery charger may have one or two ports to accept a NICAD battery pack from the DC cast saw. The batteries are placed into the charging ports for recharging. The charger is sized such that recharging is complete in 14 to 45 minutes. An LED is provided in front of each battery pack position on the charger. This LED will light up indicating that the battery pack is fully charged at the completion of the charged-cycle. The charger will also have a DC power outlet which will allow the unit to be connected by wire from the saw to the charger and continuously run the unit off the charger/DC power outlet. In this way the unit may possibly be operated without the battery pack attached.

The chargers described are well-known in the art and provided for a multitude of products. Any suitable charger design providing the relevant characteristics may be used with the invention.

At the forward end of the housing 1 there is provided a shroud 15 which is made of an accordion-like material. The shroud is preferably formed of silicone rubber. This shroud may alternatively be made of a sliding member which slides in a direction parallel to the plane of the blade as shown in the figures. This shroud engages the surface of a casting material upon initiation of the sawing process. As can be seen from the figures as the saw cuts through the material and is received more deeply into the material the shroud folds in an accordion style maintaining the close contact with the surface of the cast. In this way the operation of the impeller or fan 8 causes air to be drawn from the area around the blade, however, the shroud has sealed most of the area around the blade forcing the air to travel through very narrow gaps between the shroud and the cast as well as the slot formed by the cutting action of the blade. In this way, the area most ladened with debris (the area near the cutting operation) has the largest quantity of air drawn through it and reduces the amount of overspill of dust and debris into the ambient atmosphere and reduces the need for large volumes of air to be drawn from the blade in order to entrain the debris from a distance.

A representative fan operates to draw 10 cubic feet per minute of air at 14,400 rpm.

A pressure switch 16 is provided to sense the quantity of force being applied to the saw blade. If an increase in force is applied to the saw blade the increase in pressure on the pressure switch causes the pressure switch to cause an increase in the current supplied to the electric motor 3. This pressure switch operates through suitable circuitry that is well known. Thus,, the built in pressure sensitive switch is wired directly to the motor to provide this increase in current when necessary. The switch causes an increase in the current to the motor proportional to the force sensed upon the blade. This advantage enables the torque to be increased dependent on the toughness of the casting material. The result is increased time between battery recharges due to permitting the motor to idle at a lower speed with lower applied pressure and also increases the motor life.

What is claimed is:

1. A saw for removing orthopaedic casting bandages comprising:

a) a housing;

b) an electric motor within said housing having a rotating shaft;

c) a saw blade operated by said rotating shaft;

d) a blower within said housing for pulling a flow of ambient air around said blade to a collection volume for collecting debris created during a sawing operation; and, e) a shroud for forming a seal with a surface to enhance dust collection, said shroud movable between a first position covering a portion of said saw blade and a second position exposing said portion of said saw blade, said shroud being linearly retractably movable from said first position to said second position by interference of a casting bandage during a cutting operation.

2. The saw according to claim 1 wherein said saw blade is operated by said rotating shaft through a transmission gear.

3. The saw according to claim 1 including a battery pack received by said housing through a coupling to electrically connect said battery pack to said motor to supply electricity to said motor.

4. The saw according to claim 3 wherein said battery pack is removable from said housing.

5. The saw according to claim 4 wherein said battery pack is rechargeable using ordinary household current.

6. The saw according to claim 4 wherein said battery pack is received at least partially within an opening defined by said housing.

7. A cast saw for removing orthopaedic bandages comprising:
   a) a housing;
   b) an electric motor mounted within said housing for operating a saw blade;
   c) a transmission for transmitting power from said motor to a blade operatively mounted to said housing;
   d) a rechargeable battery pack for supplying electricity to said motor;
   e) a debris path defined by said housing extending from said blade to a collection chamber; and
   f) said collection chamber is removably received within said housing.

8. The cast saw according to claim 7 wherein the battery pack is received within said housing.

* * * * *